(12) United States Patent
Shoemaker

(10) Patent No.: US 7,501,254 B2
(45) Date of Patent: Mar. 10, 2009

(54) METHODS AND COMPOSITIONS FOR AMPLIFICATION AND CAPTURE OF NUCLEIC ACID SEQUENCES

(75) Inventor: Daniel D. Shoemaker, San Diego, CA (US)

(73) Assignee: GHC Technologies, Inc., La Jolla, CA (US)

( * ) Notice: Subject to any disclaimer, the term of this patent is extended or adjusted under 35 U.S.C. 154(b) by 20 days.

(21) Appl. No.: 11/879,966

(22) Filed: Jul. 19, 2007

(65) Prior Publication Data

US 2008/0171364 A1 Jul. 17, 2008

Related U.S. Application Data

(60) Provisional application No. 60/832,049, filed on Jul. 20, 2006, provisional application No. 60/921,796, filed on Apr. 4, 2007.

(51) Int. Cl.
*C12Q 1/68* (2006.01)
*C12P 19/34* (2006.01)

(52) U.S. Cl. .................. 435/6; 435/91.1; 435/91.2

(58) Field of Classification Search .............. None
See application file for complete search history.

(56) References Cited

U.S. PATENT DOCUMENTS

| | | | |
|---|---|---|---|
| 4,994,368 A | 2/1991 | Goodman et al. |
| 5,011,769 A | 4/1991 | Duck et al. |
| 5,112,734 A | 5/1992 | Kramer et al. |
| 5,270,184 A | 12/1993 | Walker et al. |
| 5,273,879 A | 12/1993 | Goodman et al. |
| 5,356,774 A | 10/1994 | Axelrod et al. |
| 5,397,698 A | 3/1995 | Goodman et al. |
| 5,418,149 A | 5/1995 | Gelfand et al. |
| 5,471,676 A | 11/1995 | Muraishi |
| 5,591,609 A | 1/1997 | Auerbach |
| 5,648,211 A | 7/1997 | Fraiser et al. |
| 5,674,679 A | 10/1997 | Fuller |
| 5,712,124 A | 1/1998 | Walker |
| 5,741,640 A | 4/1998 | Fuller |
| 5,744,311 A | 4/1998 | Fraiser et al. |
| 5,756,285 A | 5/1998 | Fuller |
| 5,814,492 A | 9/1998 | Carrino et al. |
| 5,824,517 A | 10/1998 | Cleuziat et al. |
| 5,908,744 A | 6/1999 | McAllister et al. |
| 6,033,881 A | 3/2000 | Himmler et al. |
| 6,087,133 A | 7/2000 | Dattagupta et al. |
| 6,124,120 A | 9/2000 | Lizardi |
| 6,143,495 A | 11/2000 | Lizardi |
| 6,180,338 B1 | 1/2001 | Adams |
| 6,207,368 B1 | 3/2001 | Adams |
| 6,214,587 B1 | 4/2001 | Dattagupta et al. |
| 6,225,062 B1 | 5/2001 | Dunn et al. |
| 6,225,067 B1 | 5/2001 | Rogers |
| 6,248,567 B1 | 6/2001 | Liles et al. |
| 6,251,639 B1 | 6/2001 | Kurn |
| 6,255,082 B1 | 7/2001 | Lizardi |
| 6,261,808 B1 | 7/2001 | Auerbach |
| 6,280,949 B1 | 8/2001 | Lizardi |
| 6,642,034 B2 | 11/2003 | Lizardi |
| 6,686,156 B2 | 2/2004 | Kurn |
| 6,692,918 B2 | 2/2004 | Kurn |
| 6,716,580 B2 | 4/2004 | Gold et al. |
| 6,821,734 B2 | 11/2004 | Kambara et al. |
| 6,825,010 B2 | 11/2004 | Spier et al. |
| 6,972,174 B2 | 12/2005 | Xue et al. |
| RE38,960 E | 1/2006 | Dattagupta et al. |
| 6,994,963 B1 | 2/2006 | Murphy et al. |
| RE39,007 E | 3/2006 | Dattagupta et al. |
| 7,074,600 B2 | 7/2006 | Dean et al. |
| 2001/0036629 A1 | 11/2001 | Dower et al. |
| 2002/0058270 A1 | 5/2002 | Kurn |
| 2002/0137036 A1 | 9/2002 | Sorge et al. |
| 2002/0187477 A1 | 12/2002 | Xue et al. |
| 2003/0017487 A1 | 1/2003 | Xue et al. |
| 2003/0044779 A1 | 3/2003 | Goelet et al. |
| 2003/0082572 A1 | 5/2003 | Spier et al. |
| 2003/0087271 A1 | 5/2003 | Ebersole et al. |
| 2003/0104430 A1 | 6/2003 | Nerenberg et al. |
| 2003/0104431 A1 | 6/2003 | Van Ness et al. |
| 2003/0143536 A1 | 7/2003 | Lizardi |
| 2003/0143587 A1 | 7/2003 | Dean et al. |

(Continued)

FOREIGN PATENT DOCUMENTS

EP  0300796 A2  1/1989

(Continued)

OTHER PUBLICATIONS

Nelson, Scott W; Yang, Jingsong; Benkovic, Stephen J, Site-directed Mutations of T4 Helicase Loading Protein (gp59) Reveal Multiple Modes of DNA Polymerase Inhibition and the Mechanism of Unlocking by gp41 Helicase, Journal of Biological Chemistry, Mar. 31, 2006, pp. 8697-8706, vol. 281, No. 13, Stanford University, University Park, PA 16802, US.

(Continued)

*Primary Examiner*—Young J Kim
(74) *Attorney, Agent, or Firm*—Roeder & Broder LLP; James P. Broder

(57) ABSTRACT

Methods for amplification and capture of nucleic acid sequences include annealing a forward primer to a DNA or RNA template in a first reaction vessel including fewer than four different dNTPs; forming an extended primer that terminates when an omitted dNTP is required for further extension; releasing the extended primer; exponentially amplifying the extended primer in a second reaction vessel that includes a reverse primer, four different dNTPs and a capture probe that includes n oligonucleotides having fewer than n locking nucleic acids; and concurrently capturing one of the extended primers with the capture probe while amplifying the extended primer. The steps of annealing, extending and releasing can occur at a first reaction temperature that is substantially isothermal and in the absence of a helicase. The steps of exponentially amplifying and capturing can occur at a second reaction temperature that is substantially isothermal.

45 Claims, 8 Drawing Sheets

U.S. PATENT DOCUMENTS

| | | |
|---|---|---|
| 2003/0190627 A1 | 10/2003 | Zhao et al. |
| 2003/0207292 A1 | 11/2003 | Notomi et al. |
| 2004/0038258 A1 | 2/2004 | Harley et al. |
| 2004/0063144 A1 | 4/2004 | Lizardi et al. |
| 2004/0175729 A1 | 9/2004 | Hiyama |
| 2004/0203019 A1 | 10/2004 | Kurn |
| 2004/0203025 A1 | 10/2004 | Kurn |
| 2004/0234996 A1 | 11/2004 | Hanna |
| 2004/0248105 A1 | 12/2004 | Kumar |
| 2005/0095610 A1 | 5/2005 | Kuo et al. |
| 2005/0164213 A1 | 7/2005 | Tabor et al. |
| 2005/0239109 A1 | 10/2005 | Hurt |
| 2005/0260573 A1 | 11/2005 | Rabbani et al. |
| 2006/0084068 A1 | 4/2006 | Johnson |
| 2006/0099607 A1 | 5/2006 | Nakashima et al. |
| 2006/0115838 A1 | 6/2006 | Bazar et al. |
| 2006/0160084 A1 | 7/2006 | Mitani et al. |
| 2006/0160108 A1 | 7/2006 | Romanov et al. |
| 2006/0166250 A1 | 7/2006 | Brenner |
| 2006/0172333 A1 | 8/2006 | Chen |

FOREIGN PATENT DOCUMENTS

| | | | |
|---|---|---|---|
| EP | 0826779 | A1 | 3/1998 |
| EP | 0971039 | A2 | 1/2000 |
| EP | 1275715 | A1 | 1/2003 |
| JP | 10066589 | | 3/1998 |
| WO | WO-90/14439 | T | 11/1990 |
| WO | WO-91/01384 | | 2/1991 |
| WO | WO-91/04340 | | 4/1991 |
| WO | WO-92/01813 | | 2/1992 |
| WO | WO-95/03430 | | 2/1995 |
| WO | WO-95/25180 | | 9/1995 |
| WO | WO-96/17079 | | 6/1996 |
| WO | WO-96/23904 | A1 | 8/1996 |
| WO | WO9727331 | | 7/1997 |
| WO | WO-98/11255 | | 3/1998 |
| WO | WO-99/18241 | | 4/1998 |
| WO | WO-98/38296 | | 9/1998 |
| WO | WO-00/28084 | A1 | 5/2000 |
| WO | WO-00/41524 | A2 | 7/2000 |
| WO | WO-00/41524 | A3 | 7/2000 |
| WO | WO-00/62036 | A1 | 10/2000 |
| WO | WO-00/70095 | A2 | 11/2000 |
| WO | WO-00/70095 | A3 | 11/2000 |
| WO | WO01/20035 | | 3/2001 |
| WO | WO-02/46456 | A1 | 6/2002 |
| WO | WO-02/061145 | A2 | 8/2002 |
| WO | WO-03/008642 | A2 | 1/2003 |
| WO | WO-03/008642 | A3 | 1/2003 |
| WO | WO-03/054233 | A1 | 7/2003 |
| WO | WO-03/080645 | A2 | 10/2003 |
| WO | WO-03/093500 | A1 | 11/2003 |
| WO | WO-2004/027025 | A2 | 4/2004 |
| WO | WO-2004/055197 | A2 | 7/2004 |
| WO | WO-2004/058987 | A2 | 7/2004 |
| WO | WO-2004/058987 | A3 | 7/2004 |
| WO | WO-2004/063700 | A2 | 7/2004 |
| WO | WO-2005/016251 | A2 | 2/2005 |
| WO | WO-2005/016251 | A3 | 2/2005 |
| WO | WO-2005/030929 | A2 | 4/2005 |
| WO | WO-2005/030983 | A2 | 4/2005 |
| WO | WO-2005/047462 | A2 | 5/2005 |
| WO | WO-2005/089508 | A2 | 9/2005 |
| WO | WO-2005/118853 | A2 | 12/2005 |
| WO | WO-2005/118853 | A3 | 12/2005 |
| WO | WO-2005/123961 | A2 | 12/2005 |
| WO | WO-2005/123961 | A3 | 12/2005 |
| WO | WO-2006/026388 | A2 | 3/2006 |

OTHER PUBLICATIONS

Lizardi, P. M.; Kramer, F. R.; Exponential Amplification of Nucleic Acids: New Diagnostics using DNA Polymerases and RNA Replicases, Trends in Biotechnology, Feb. 1990, pp. 53-58, vol. 9, No. 2, London, UK.

Walker, G.Terrance ; Empirical Aspects of Strand Displacement Amplification, PCR Methods Appl., Aug. 1993, pp. 1-6, vol. 3, Issue 1, Becton Dickinson Research Center, Research Triangle Park, North Carolina 22709-2016, US.

Nycz, C.M. et al.; Quantitive Reverse Transcription Strand Displacement Amplification: Quantitation of Nucleic Acids Using an Isothermal Amplification Technique, Anal. Biochemistry, Jun. 1, 1998, pp. 226-234, Dept. of Molecular Biology, Becton Dickinson Research Center, Research Triangle Park, North Carolina 22709-2016, US.

Walker, G.T. et al. ; A DNA Probe Assay Using Strand Displacement Amplification (SDA) and Filtration to Separate Reacted and Unreacted Detector Probes, National Library of Medicine, NDN-237-1079-6976-6, Molecular Cell Probes Journal, Dec. 1995, pp. 399-403, Academic Press, US.

Walker, G.T. et al.; DNA Detection by Strand Displacement Amplification and Fluorescence Polarization with Signal Enhancement using a DNA binding protein, Nucleic Acids Research Journal, Jan. 15, 1996, pp. 348-353, vol. 24, Issue 2, Becton Dickinson Research Center, Research Triangle Park, North Carolina 22709-2016, US.

Walker, G.Terrance et al; Strand displacement amplification—an isothermal, in vitro DNA Amplification Technique, Nucleic Acids Research, Apr. 11, 1992, pp. 1691-1696, vol. 20, Issue 7, 1992 Oxford University Press US.

Walker, G.T. et al.; Isothermal in vitro amplification of DNA by a restriction enzyme/DNA polymerase system, Proc National Academy Science USA Journal, Jan. 1, 1992, pp. 392-396, vol. 89, Issue 1, Dept. of Molecular Biology, Becton Dickinson Research Center, Research Triangle Park, North Carolina 22709-2016, US.

Zevin-Sonkin, D. et al.; DENS (differential extension with nucleotide subsets): application to the sequencing of human genomic DNA and cDNA, DNA Sequence 1999, pp. 245-254, Department of Structural Biology, Weizmann Institute of Science, Rehovot, Israel.

Lvovksy, L. et al.; Interdependence between DNA template secondary structure and priming efficiencies of short primers, Nucleic Acids Research, Dec. 1, 1998, pp. 5525-5532, Department of Structural Biology, Weizmann Institute of Science, Rehovot 76100, Israel.

Estrada, G. et al.Sequence-specific detection of PCR-amplified DNA by restriction enzyme release of hybrids, Molecular and Cellular Probes Journal, 1996, pp. 179-185, vol. 10, Issue 3, Department of Molecular Recognition and Structural Biology, Univerisad Nacional Autonoma de Mexico, Cuernavaca, Morelos, Mexico.

Kramer, F. R. and Lizardi, P. M.; Amplifiable Hybridization Probes, National Library of Medicine, NDN-238-0844-0319-1, Ann. Biol. Clin., 1990, pp. 409-411, vol. 48, issue 6, Paris, France.

Lomell, H.; Lizardi, P. M. et al.; Quantitative Assays Based on the use of Replicatable Amplifiable Hybridization Probes, National Library of Medicine, NDN-238-0802-5109-9, Clinical Chemistry, Sep. 1989, pp. 1826-1831, vol. 35, issue 9, Clin. Chem. US.

Nimonkar, Amitabh V. and Boehmer, Paul E; Reconstitution of recombination-dependent DNA synthesis in herpes simplex virus 1, PNAS, Sep. 2, 2003, vol. 100, No. 18, pp. 10201-10206, Department of Biochemistry and Molecular Biology, University of Miami School of Medicine, Miami FL 33101-6129, US.

Elias-Arnanz, Montserrat and Salas, Margarita, Bacteriophage ø29 DNA replication arrest caused by codirectional collisions with the transcription machinery, The EMBO Journal, vol. 16, No. 18, pp. 5775-5783, 1997; Oxford University Press, US.

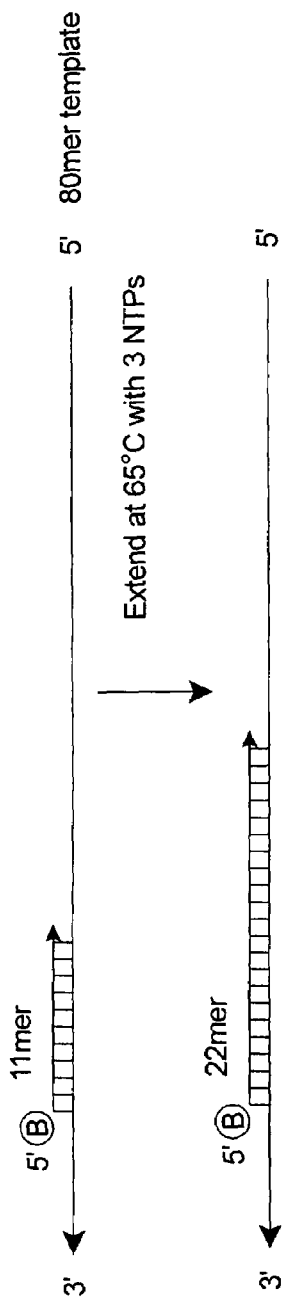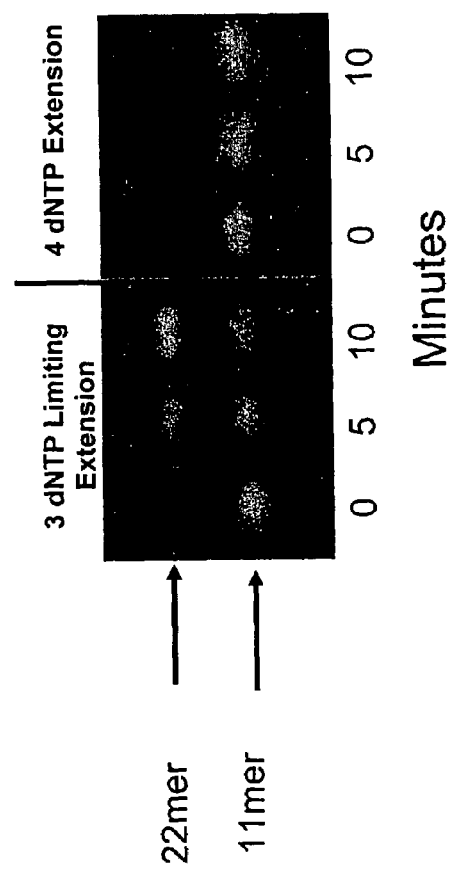
Fig. 3A
Fig. 3B

SEQUENCE LISTING

```
<160> NUMBER OF SEQ ID NOS: 8

<210> SEQ ID NO 1
<211> LENGTH: 43
<212> TYPE: DNA
<213> ORGANISM: Artificial
<220> FEATURE:
<223> OTHER INFORMATION: Segment of DNA or RNA template.  Segment
      includes primer binding site and primer extension binding site
      devoid of dTTP.

<400> SEQUENCE: 1
tcttcgtggc cttcagaggc acggtcgtcg gcgccattat gcc                    43

<210> SEQ ID NO 2
<211> LENGTH: 11
<212> TYPE: DNA
<213> ORGANISM: Artificial
<220> FEATURE:
```

```
<223> OTHER INFORMATION: Primer extension binding site of DNA or RNA
      template.  Binding site is devoid of "T".

<400> SEQUENCE: 2
cagaggcacg g                                                              11

<210> SEQ ID NO 3
<211> LENGTH: 11
<212> TYPE: DNA
<213> ORGANISM: Artificial
<220> FEATURE:
<223> OTHER INFORMATION: Primer binding site on the DNA or RNA template.

<400> SEQUENCE: 3
tcgtcggcgc c                                                              11

<210> SEQ ID NO 4
<211> LENGTH: 11
<212> TYPE: DNA
<213> ORGANISM: Artificial
<220> FEATURE:
<223> OTHER INFORMATION: Primer sequence complementary to primer binding
      site on DNA or RNA template.

<400> SEQUENCE: 4
ggcgccgacg a                                                              11

<210> SEQ ID NO 5
<211> LENGTH: 22
<212> TYPE: DNA
<213> ORGANISM: Artificial
<220> FEATURE:
<223> OTHER INFORMATION: Extended primer which includes the primer and
      an extension segment that is complementary to the primer extension
      binding site on the DNA or RNA template.

<400> SEQUENCE: 5
ggcgccgacg accgtgcctc tg                                                  22

<210> SEQ ID NO 6
<211> LENGTH: 16
<212> TYPE: DNA
<213> ORGANISM: Artificial
<220> FEATURE:
<223> OTHER INFORMATION: Capture probe sequence.

<400> SEQUENCE: 6
ggcattcacg atttcc                                                         16

<210> SEQ ID NO 7
<211> LENGTH: 22
<212> TYPE: DNA
<213> ORGANISM: Artificial
<220> FEATURE:
<223> OTHER INFORMATION: Extended primer following amplification.

<400> SEQUENCE: 7
cattctggaa atcgtcaatg cc                                                  22

<210> SEQ ID NO 8
<211> LENGTH: 11
<212> TYPE: DNA
<213> ORGANISM: Artificial
<220> FEATURE:
<223> OTHER INFORMATION: Unextended primer sequence.
```

-continued

```
<400> SEQUENCE: 8
cattctggaa a                                                              11
```

METHODS AND COMPOSITIONS FOR AMPLIFICATION AND CAPTURE OF NUCLEIC ACID SEQUENCES

RELATED APPLICATIONS

This Application claims domestic priority on U.S. Provisional Application Ser. No. 60/832,049, filed on Jul. 20, 2006, and on U.S. Provisional Application Ser. No. 60/921,796, filed on Apr. 4, 2007. The contents of U.S. Provisional Application Ser. Nos. 60/832,049 and 60/921,796 are incorporated herein by reference to the extent permitted.

BACKGROUND

Deoxyribonucleic acid (DNA) and ribonucleic acid (RNA) each utilizes four bases in a particular sequence to form genetic information. DNA uses adenine [A], guanine [G], thymine [T], and cytosine [C], while RNA uses A, G, C and Uracil (U). In both DNA and RNA, these bases are attached to a sugar-phosphate backbone having a 3' end and an opposing 5' end. When two single strands of DNA bind (associate) to form double-stranded DNA (hybridized or duplexed DNA), the 5' to 3' direction in one strand is positioned in a complementary manner, e.g., 180 degrees relative to the 5' to 3' direction of the other strand. A is complementary to T and G is complementary to C in DNA/DNA hybrids. A is complementary to U and G is complementary to C in DNA/RNA hybrids.

Amplification reactions are used to increase the number of DNA and/or RNA so that detection of specific sequences can be achieved. In certain types of amplification reactions, a relatively short sequence of DNA called a primer associates with a complementary sequence on the DNA template. A DNA polymerase uses deoxynucleoside triphosphates (dNTPs) to sequentially add nucleotides to the 3' end of the primer (also referred to herein as "extension"). For extension to occur, a 3' hydroxyl group is required on the ribose ring, which is the sugar moiety of the nucleic acid backbone. If the 3' hydroxyl group of a nucleotide is replaced with a hydrogen atom, the nucleotide is known as a dideoxynucleotide (ddNTP), and cannot support attachment of an additional base during extension.

One of the drawbacks of certain amplification reactions is creation of "negative reaction products". These negative reaction products have been found to be the result of the forward and reverse primers combining with one another to varying degrees in a template independent fashion. Although the precise mechanism for generation of this negative reaction product is not completely known, it is understood that certain reactions occur involving the primers in a forward-forward, forward-reverse or reverse-reverse configuration. These reactions can generate negative reaction products that can interfere with the accuracy of the detection process.

SUMMARY

The present invention is directed to a method for amplification and capture of nucleic acid sequences. In one embodiment, the method includes one or more of the steps of annealing a forward primer to a DNA or RNA template using fewer than four different dNTPs; extending the forward primer with the dNTPs to form an extended primer that terminates when an omitted dNTP is required for further extension of the forward primer; releasing the extended primer; exponentially amplifying the extended primer, adding a reverse primer, four different dNTPs and a capture probe, the capture probe including n oligonucleotides, wherein fewer than n of the oligonucleotides are locking nucleic acids; and concurrently capturing one of the extended primers in the reaction vessel with the capture probe while amplifying the extended primer. Further, in certain embodiments, the steps of annealing, extending and releasing occur at a first reaction temperature that is substantially isothermal and in the absence of a helicase. In addition, or alternatively, the steps of exponentially amplifying and capturing occur at a second reaction temperature that is substantially isothermal.

In certain embodiments, the steps of annealing, extending and releasing are all performed in a non-exponential manner. In one embodiment, the step of annealing includes the forward primer having approximately 11 bases. In another embodiment, the step of extending includes the extended primer having approximately 22 bases. The step of annealing can include using one ddNTP and three dNTPs that are different from one another.

In one specific embodiment, the number of bases of the capture probe (n) equals 16. Further, in one embodiment, the number of locking nucleic acids can be less than approximately 75% of n. In some embodiments, n can be greater than approximately 14 and less than approximately 18. In these and other embodiments, the number of locking nucleic acids can be greater than approximately 6 and less than approximately 12. Further, at least one of the reaction temperatures can be within the range of between approximately 60° C. and 68° C. In one specific embodiment, the reaction temperature is approximately 65° C. In certain embodiments, the first reaction temperature can be substantially similar to the second reaction temperature.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which:

FIG. 3A is a schematic diagram showing one embodiment of a portion of the initiation phase;

FIG. 3B is an illustration showing experimental results for primer extension using (i) an extension method described herein, and (ii) a negative control extension method;

DESCRIPTION

Figure 1:
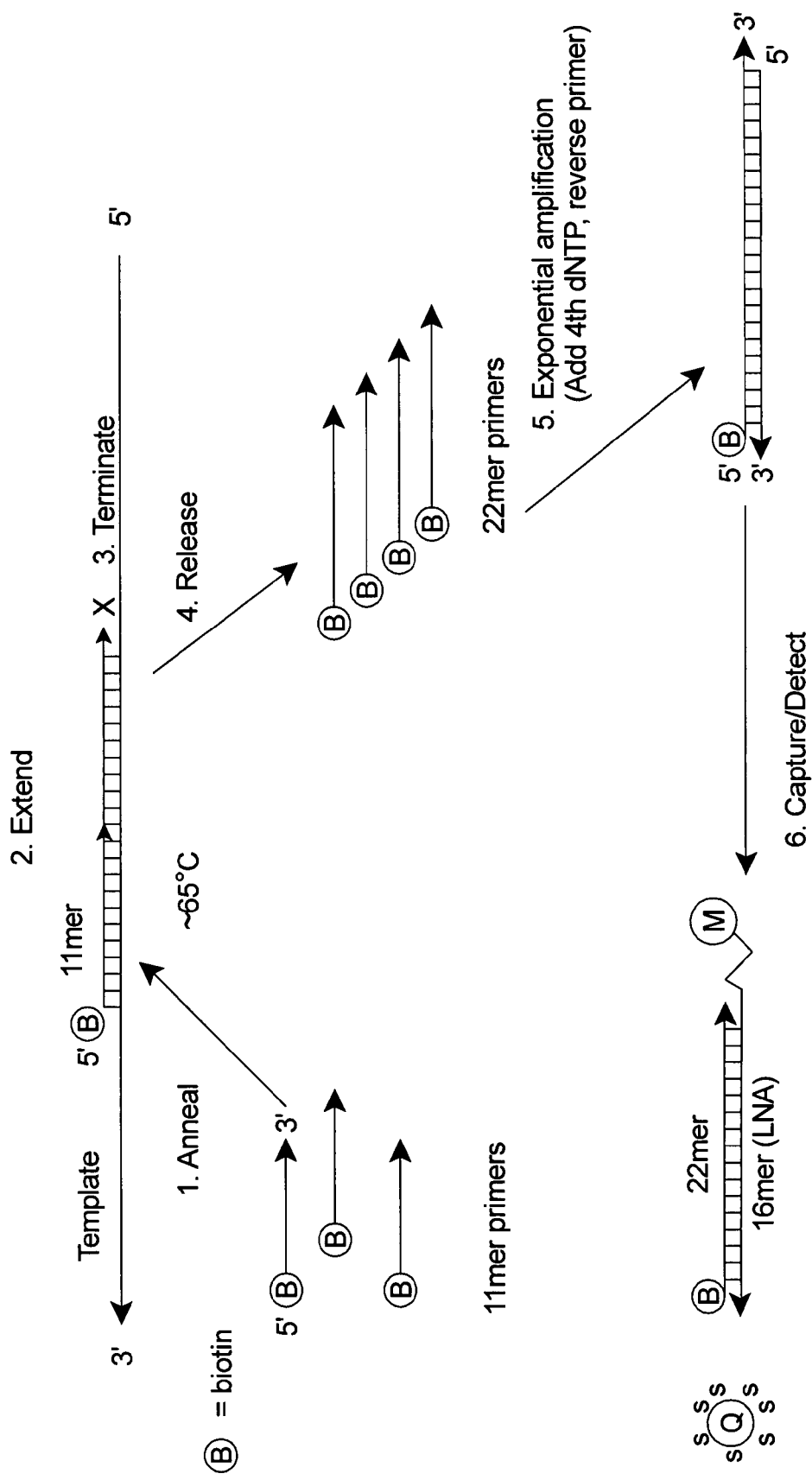
FIG. 1 is a schematic diagram illustrating one embodiment of a method for amplifying and capturing a nucleic acid sequence, including an initiation phase and an exponential amplification/capture phase.

FIG. 1 illustrates one embodiment of a two-phase method for amplification and capture of nucleic acid sequences, used for the detection of pathogens, disease-causing substances or other suitable genetic material. Although the amplification and/or capture methods provided herein are particularly suited toward substantially isothermal processes, it is recognized that one or more non-isothermal processes, e.g., temperature cycling, can be used during one or more of the steps described herein. Further, as provided herein, in certain embodiments, despite utilizing an isothermal process, it is unnecessary to use an enzyme such as a helicase to denature or otherwise dissociate the double stranded template.

In certain embodiments, the amplification and capture method includes a linear or otherwise non-exponential initiation process (indicated as steps 1-4, also sometimes referred to herein as a linear amplification phase) and a subsequent exponential amplification/capture process (indicated as steps 5-6, also sometimes referred to herein as an exponential amplification phase). As illustrated in FIG. 1, the steps during the initiation process include one or more of: (1) annealing an oligonucleotide primer (i.e. a primer that includes 11 bases or any other suitable number of bases) to a DNA or RNA template of any length, (2) extending the primer (i.e. to 22 bases or another suitable length), (3) terminating extension of the primer, and (4) releasing the extended primer. In an alternative embodiment, this initiation process can include an exponential or otherwise non-linear process. Further, in one embodiment, the initiation process occurs at a first substantially isothermal reaction temperature that can vary depending upon the reactants used and the specific reaction products to be captured, for example.

In the embodiment illustrated in FIG. 1, the single-stranded 22mers which are generated during the initiation process serve as templates for the subsequent exponential amplification phase (indicated as step 5 in FIG. 1). In one embodiment, two short oligonucleotide primers (e.g. 11mers), a polymerase, nucleotide building blocks (also sometimes referred to herein as "bases") including one or more of dATP, dTTP, dCTP and dGTP (also sometimes referred to herein simply as "A", "T", "C" and "G", respectively), and an appropriate buffer are incubated at a substantially constant temperature to facilitate amplification. During this exponential amplification, thousands or millions of the double-stranded 22 basepair products are generated. As explained in greater detail below, in certain embodiments, this exponential amplification process can be used in conjunction with other concurrent or subsequent processes such as capture procedures (indicated as step 6 in FIG. 1), as one non-exclusive example. In alternative embodiments, other methods of exponential amplification known to those skilled in the art can be utilized. In one embodiment, the exponential amplification process occurs at a second substantially isothermal reaction temperature that can vary depending upon the reactants used and the specific reaction products to be captured, for example. Further, in one embodiment, the first reaction temperature is substantially similar, nearly identical or actually identical to the second reaction temperature.

Figure 2:
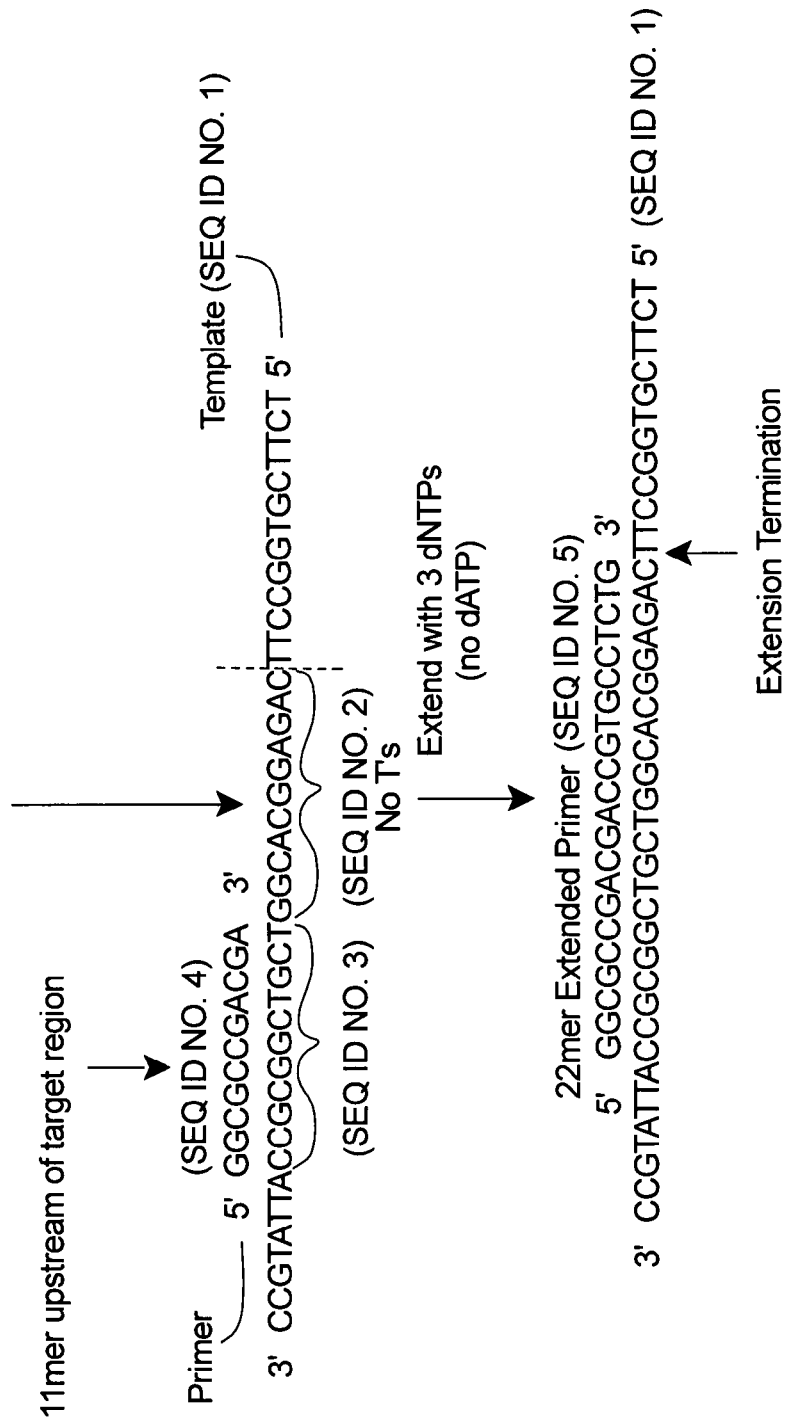
FIG. 2 is a schematic diagram showing one embodiment of a portion of the initiation phase.

FIG. 2 illustrates one non-exclusive, representative example of an embodiment of a method that is utilized during the initiation process or linear amplification process. It is understood that the specific sequences provided in the Figures and the accompanying description are provided for ease of understanding only, and that no limitations are implied by providing any particular sequence(s) of bases.

In the embodiment illustrated in FIG. 2, extension of the primer is terminated and the extended primer is released during the linear initiation phase. More specifically, a predetermined number of consecutive nucleotides that does not include one or more of the four bases is identified (i.e. 11 bases, or any other suitable number of bases) on the template (3' CCGTATTACC GCGGCTGCTG GCACGGAGAC TTCCGGTGCT TCT 5' (SEQ ID NO. 1)). In the example illustrated in FIG. 2, only the nucleotides "A", "C" and "G" (not "T") are present in the selected 11 base section (3' GGCACGGAGA C 5' (SEQ ID NO. 2)) on the template. In this embodiment, the specific 11 bases in a direction toward the 3' end of the template from the "no T" section are determined (3' CCGCGGCTGC T 5' (SEQ ID NO. 3)), and a complementary 11mer primer (5' GGCGCCGACG A 3' (SEQ ID NO. 4)) is designed to anneal to the template DNA immediately adjacent to the 11 base "no T" region.

In this example, a mixture of known amounts of each of the following are combined: the DNA (or RNA) template, the 11mer primer, a polymerase and the nucleotides complementary only to the "A", "C" and "G" (thus, only "T", "G" and "C", respectively, and no "A"). In one embodiment, during an isothermal process at a given temperature, e.g., 65° C. or another suitable temperature, the 11mer temporarily binds to the template as illustrated in FIG. 2. Once bound, the polymerase finds the 3' end of the primer and starts adding bases from the mixture that are complementary to the "no T" section of the template, as illustrated in the lower portion of FIG. 2. However, because the mixture does not include any "A" (also known as "dATP"), the bases will only be extended onto the 3' end of the primer until such time as an "A" is required, which only occurs when a "T" is next in line on the template (indicated by "extension termination" in the lower portion of FIG. 2). In this example, a 22 base extended primer (5' GGCGCCGACG ACCGTGCCTC TG 3' (SEQ ID NO. 5)) is generated because of the position of the "T" on the template. Once a 22mer is generated in this linear fashion, the 22mer can be amplified exponentially during the exponential amplification process to greatly increase the number of this 22mer, as explained in greater detail below.

In an alternative embodiment, using the above example, in addition to excluding base "A" from the reaction mixture, a dideoxynucleotide for "A" (also known as "ddATP") can be added to the reaction mixture. In this embodiment, the ddATP cannot be extended from, and the extension reaction is terminated. It is understood that depending upon the base sequence of the DNA or RNA template, one or more dideoxynucleotides (ddATP, ddTTP, ddCTP and/or ddGTP) can be included in the reaction mixture to achieve the desired termination effect.

FIGS. 3A and 3B illustrate one embodiment of the linear amplification process using a DNA template, such as an 80mer template as one non-exclusive example, and the experimental results, respectively. In this example, when only three of the nucleotides are present in the reaction mixture as described previously herein, the number of 22mer products increases over time from zero to ten minutes, as indicated by the increasing fluorescence intensity on the left portion of FIG. 3B adjacent to the "22mer" arrow. Additionally, the intensity of the fluorescence decreases on the left portion of FIG. 3B adjacent to the "11mer" arrow, demonstrating that the 11mer primers are being converted to 22mer extension products. In contrast, when all four nucleotides are included in the mixture, the number of 22mer products does not increase over time, as indicated by the lack of increase in fluorescence intensity on the right portion of FIG. 3B adjacent to the "22mer" arrow, and the substantially constant fluorescence intensity on the right portion of FIG. 3B adjacent to the "11mer" arrow.

It is recognized that although the number of bases of certain nucleotides is sometimes specified herein (i.e. 11mer, 22mer, etc.) during various methods and processes, this specificity is provided as a representative example only, and is not intended to limit the nucleotides that can be utilized with the present invention in any manner to any particular number of bases.

Referring back to FIG. 1, as illustrated following the exponential amplification step (5), depending upon the temperature of the reaction mixture, some quantity of the DNA or RNA products formed can be double stranded (e.g. 22 base pairs). For certain subsequent processes such as capturing and detection, it is desirable for these DNA or RNA products to be denatured. Denaturing of these products can occur by increasing the temperature of the products, or by maintaining a predetermined temperature (or temperature range) that is dependent upon the melting temperature (also sometimes referred to herein as "$T_m$") of the product.

Figure 4:
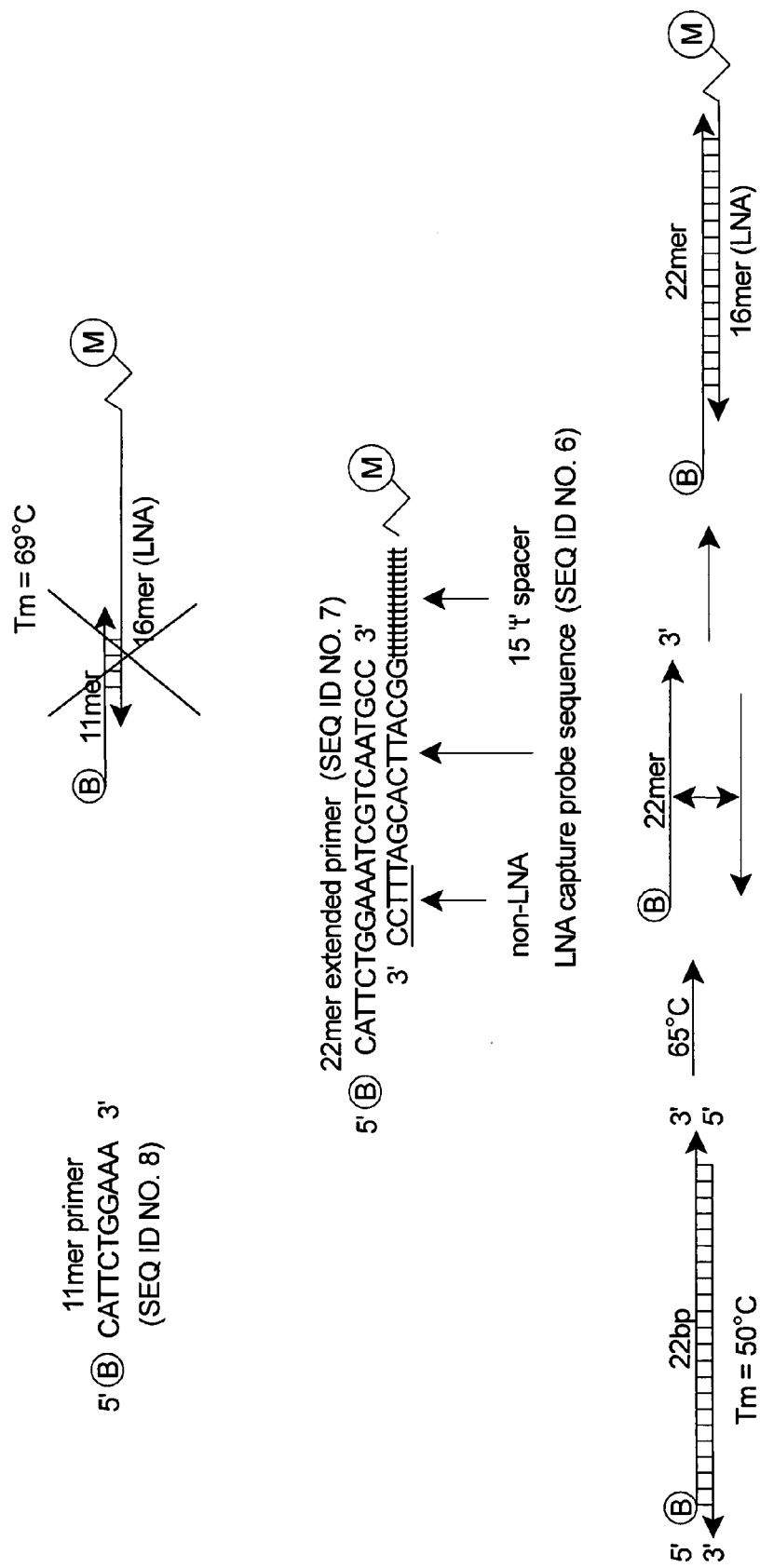
FIG. 4 is a schematic diagram showing one embodiment of the exponential amplification/capture phase.

FIG. 4 illustrates one embodiment of a method for capturing the amplified reaction products, which in this non-exclusive example are 22mer products. In this embodiment, one or more capture probes (illustrated as "16mer (LNA)" in FIG. 4) are used to capture the desired dissociated strand (having a biotin marker indicated by a B in a circle) of the amplified 22mer product either during or following the exponential amplification step. The capture probes include a series of bases that are complementary to at least a portion of the 22mer product.

In one embodiment, the capture probes can directly or indirectly be attached to magnetic beads (indicated as an "M" in a circle), as one non-exclusive example. In the embodiment illustrated in FIG. 4, the capture probe are indirectly attached to magnetic beads using a spacer (indicated by a plurality of "t"'s) is present between the magnetic bead and the 16mer capture probe (GGCATTCACG ATTTCC 3' (SEQ ID NO. 6)) so that the capture probe is better positioned and more accessible for capturing the desired reaction product (5' (biotin marker) CATTCTGGAA ATCGTCAATG CC 3' (SEQ ID NO. 7)).

In this example, at 65° C. (other suitable temperatures can be used), the double stranded 22mer becomes denatured, and the desired single-stranded target can bind to the capture probe. In certain embodiments, the capture probes can include one or more locked nucleic acids (LNA's). One example of a more detailed explanation of LNA's can be found in publications known to those skilled in the art, including, but not limited to "Locked Nucleic Acids (LNA) (Ørum, H., Jakobsen, M. H., Koch, T., Vuust, J. and Borre, M. B. (1999) Detection of the Factor V Leiden Mutation by Direct Allele-specific Hybridization of PCR Amplicons to Photoimmobilized Locked Nucleic Acids. Clin Chem., 45:1898-1905)", the publication of which is incorporated herein by reference to the extent permitted.

In some embodiments, the number and/or positioning of the LNA's can influence the melting temperature of the capture probe. Depending upon the melting temperature of the capture probe relative to the melting temperature of the DNA or RNA product, an isothermal process at a predetermined temperature can occur that allows both denaturing of the double stranded product and capture of the desired strand by the capture probe at substantially the same time, in the same reaction vessel. In certain embodiments, the capture probe includes a sufficient number of locking nucleic acids to allow efficient capture of the reaction products from the isothermal amplification reaction without requiring a separate denaturing step. As illustrated in FIG. 4, in various embodiments, an LNA capture sequence is utilized that is complementary to at least a portion of the 22mer formed during amplification.

In certain embodiments, the reaction temperature is set high enough so that the labeled 11mer primers (such as 5' (biotin marker) CATTCTGGAA A 3' in FIG. 4 (SEQ ID NO. 8)) do not bind to the capture probes on the magnetic beads. In other words, the capture probes can be specifically designed to have little or no complementary overlap between the bases on the capture probe and the bases of the 11mer primer. In general, the less overlap that is present, the lower the binding energy between the primer and the capture probe.

Alternatively, or in addition, the sequence of the capture probe is predetermined to generate a relatively low binding energy so that the 11mer primers are inhibited from binding with the capture probe in the first instance. In contrast, when the 22mer reaction product binds to the capture probe, sufficient homology exists to cause a greater level of binding energy. This increased binding energy ultimately generates a bead signal that can be readily detected by methods known to those skilled in the art.

The number of LNA's in the capture probe is adequate enough to allow efficient hybridization to occur at the elevated reaction temperature used for the isothermal amplification reaction. Alternatively, other types of modified nucleotide analogs (e.g PNA's) can be used to increase the binding energy of the capture probes above the isothermal reaction temperature.

Figure 5A:
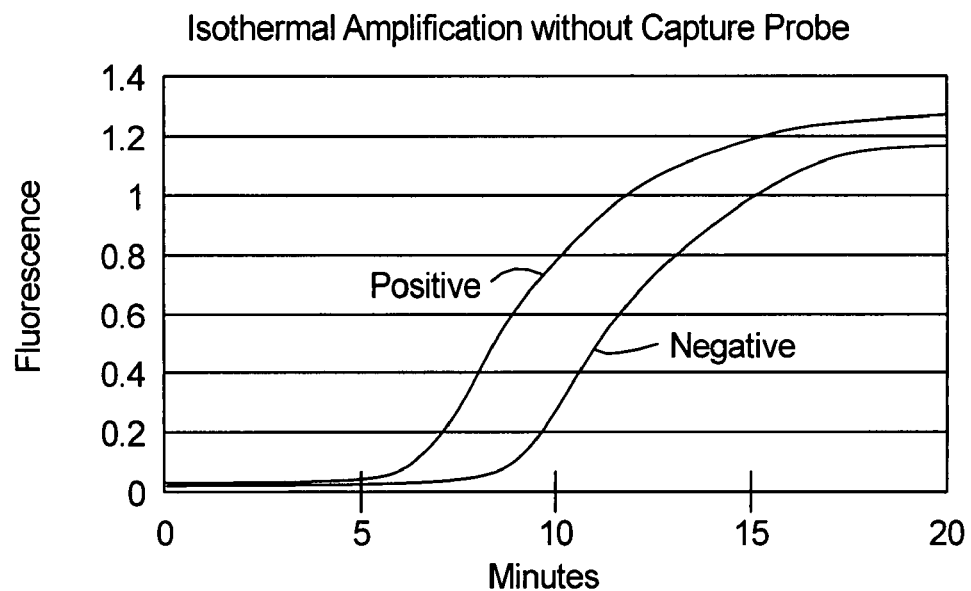
FIG. 5A is a graph illustrating fluorescence as a function of time for both positive and negative reaction products when capture probes are excluded from the reaction vessel during exponential amplification.
Figure 5B:
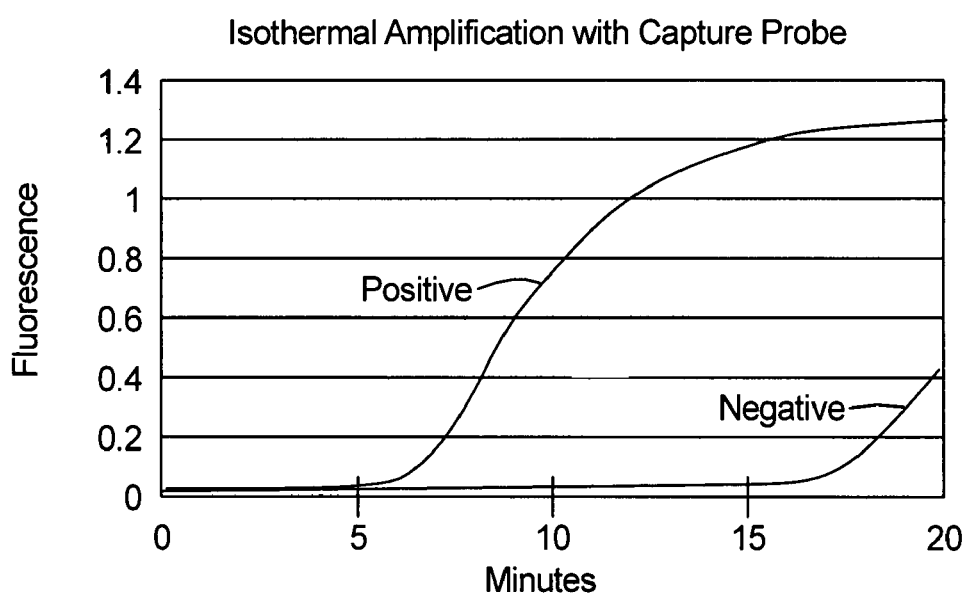
FIG. 5B is a graph illustrating fluorescence as a function of time for both positive and negative reaction products when capture probes are included in the reaction vessel during exponential amplification.

FIGS. 5A and 5B are graphs which illustrate several potential advantages of including the magnetic capture beads in the exponential isothermal amplification reaction. As provided previously, one drawback of certain amplification reactions is creation of the negative reaction products, which are believed to be caused by forward and reverse primers combining with one another to varying degrees in a template independent fashion. In contrast, positive reaction products are the desired amplified product from the initiation amplification phase.

In certain embodiments, by including the magnetic capture beads with attached capture probes in the reaction mixture during isothermal amplification, generation of the negative reaction products is inhibited. FIG. 5A illustrates an isothermal amplification in which the capture probes were not included in the reaction mixture. In this isothermal amplification reaction, the generation of the undesirable negative reaction product(s) occurs relatively close in time to generation of the desirable positive reaction product. Thus, in this type of isothermal amplification reaction, it is difficult to accurately discriminate between the positive and negative reaction products.

However, in FIG. 5B, the capture probes were included in the isothermal amplification reaction, thereby suppressing the undesired negative reaction products. Although the mechanism of the background suppression effect is not completely understood at this time, it is believed that low levels of negative reaction products can be bound by the capture probes before these negative reaction products can engage in the exponential amplification process. As a result, the negative reaction has been found to be inhibited and/or delayed as illustrated in FIG. 5B. Because of this greater time separation between generation of the positive and negative reaction products, the reaction can be strategically terminated prior to generation of any significant amount of negative reaction products, with little or no loss of generation of the positive reaction product. Consequently, the accuracy of detection of the actual presence of one or more nucleic acid sequences is enhanced.

In an alternative embodiment, capture probes that are specific to the negative reaction product(s) can be utilized to effectively suppress proliferation of the negative reaction products. These capture probes that target the negative reaction products are also referred to herein as "suppression probes". The suppression probes can be added either during or after the isothermal amplification process. Therefore, one or more different suppression probes can be used to specifically target and capture the different negative reaction products that may be formed during isothermal amplification before these negative reaction products can exponentially amplify. With this design, a smaller amount of negative reaction product will be generated, thus yielding a more accurate detection of the actual nucleic acid sequences present.

Figure 6:
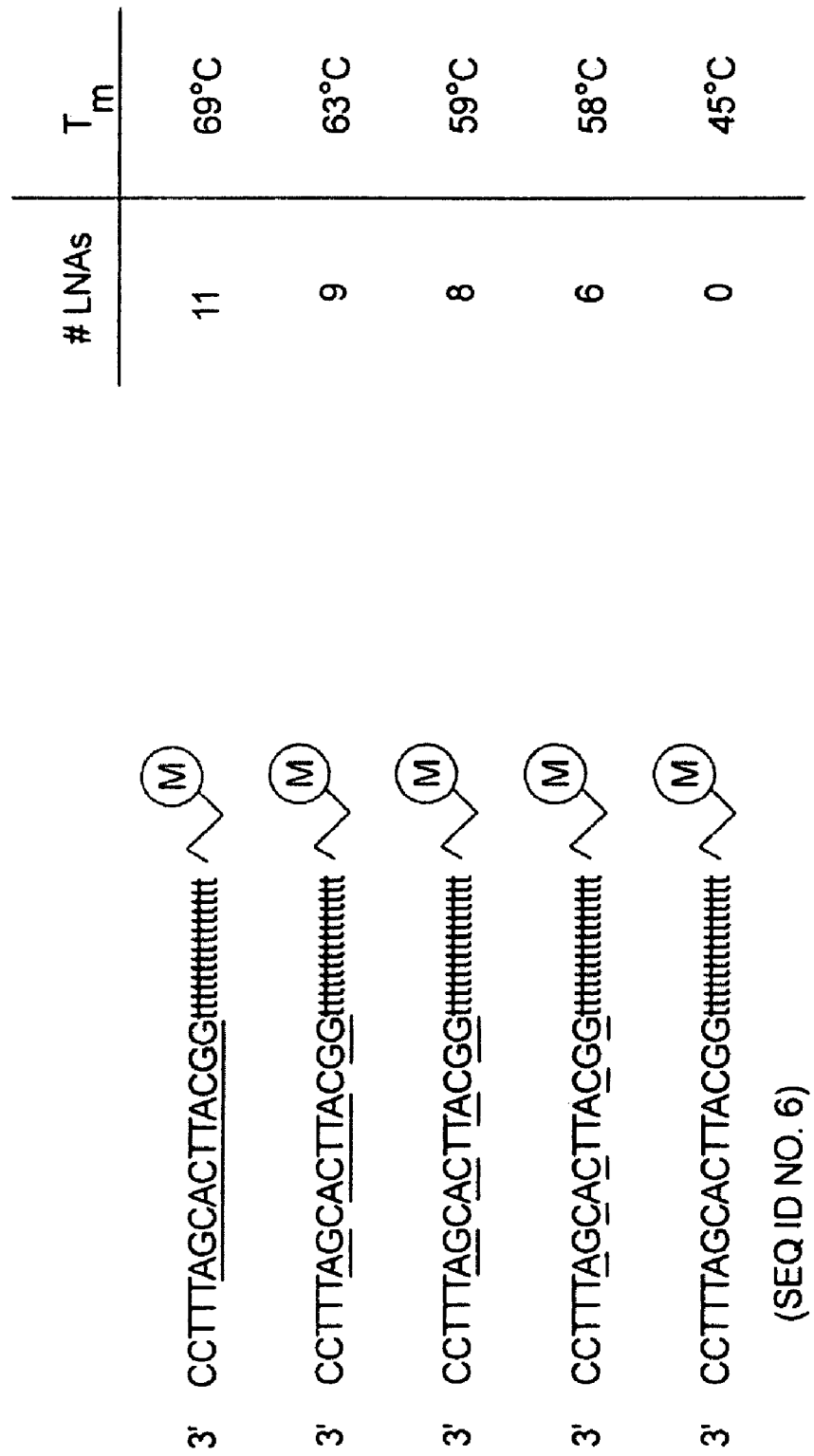
FIG. 6 is a schematic diagram showing one embodiment of exponential amplification/capture, including five different proportions of locking nucleic acids included in the capture probe.

FIG. 6 illustrates a correlation between the number of LNA's utilized in a capture probe and the $T_m$ of the capture probe. In this example, a 16mer capture probe (5' GGCATTCACG ATTTCC 3' (SEQ ID NO. 6)) is utilized, although it is recognized that capture probes having greater or fewer than 16 bases can be used. On the left side of FIG. 6, the locked nucleic acids are underlined. In this example, the greater the number of LNA's in the capture probe, the greater the $T_m$ of the capture probe. By altering the $T_m$ of the capture probe relative to the $T_m$ of the 22mer to be captured, the efficiency of the capturing process can be influenced depending upon the reaction temperature, as provided in greater detail below.

Figure 7A:
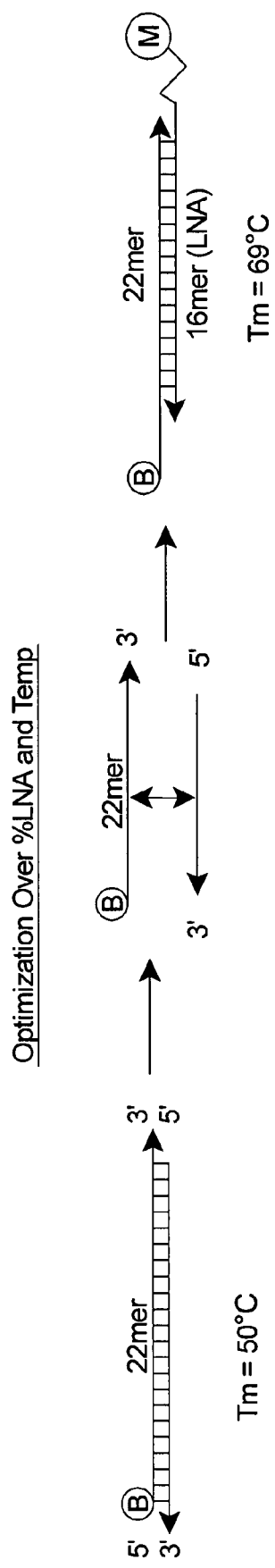
FIG. 7A is a schematic diagram showing one embodiment of a portion of the capture process during or following exponential amplification.

FIG. 7A shows one embodiment of a portion of the capture process. In this embodiment, the $T_m$ of the 16mer LNA capture probe is 69° C., and the $T_m$ of the 22mer reaction product is 50° C. In one embodiment, the 16mer capture probe illustrated in FIG. 7A can include 11 LNA's, such as the 11 LNA capture probe illustrated in FIG. 6, as one non-exclusive representative example. It is recognized, however, the depending upon the base sequence of the capture probe, as well as the percentage of LNA's used in the capture probe, LNA capture probes having sequences other than that shown in FIG. 6 can be used to achieve the desired $T_m$ of the capture probe for the particular reaction product being captured.

Figure 7B:
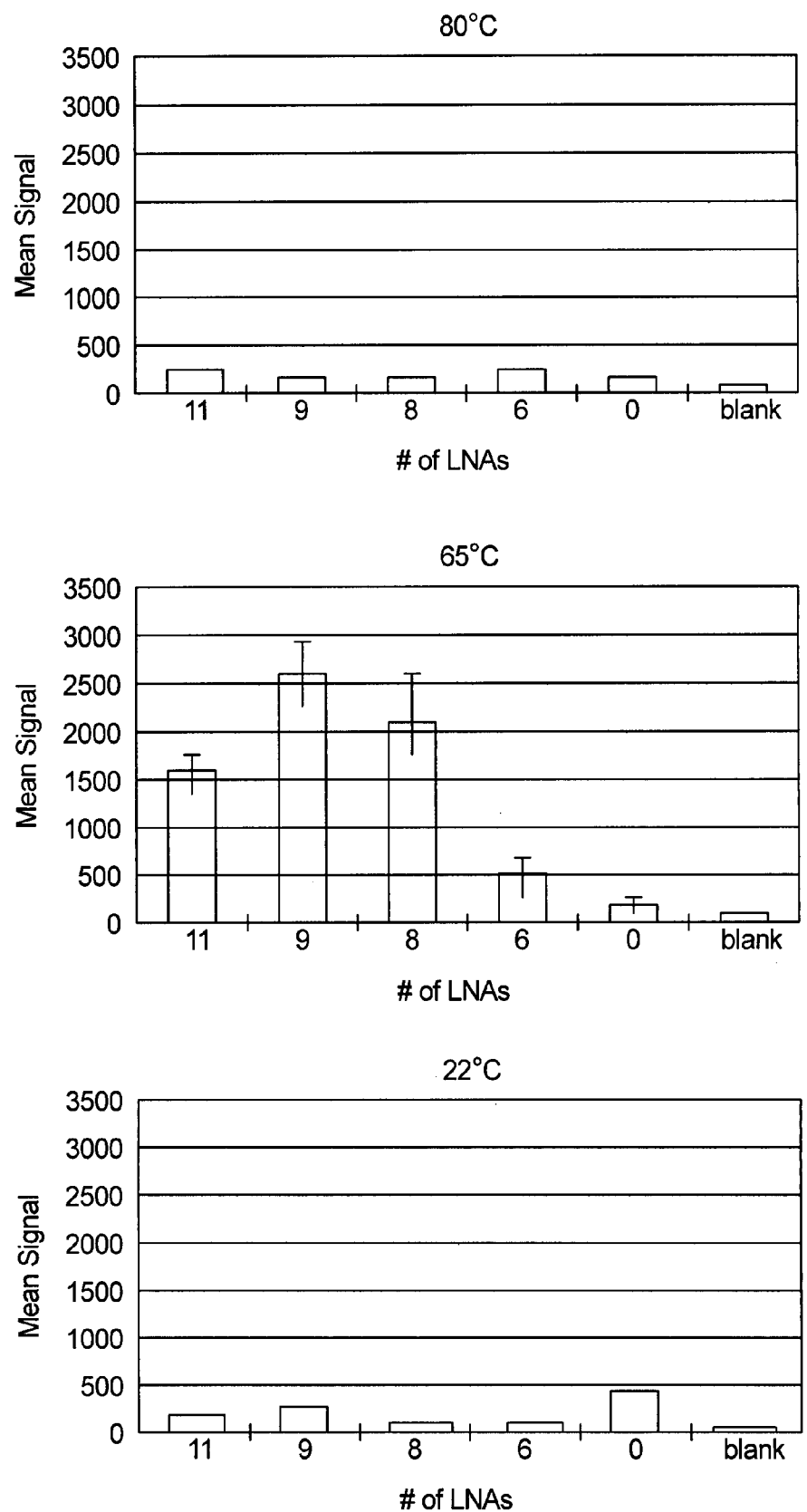
FIG. 7B shows three graphs of the extent of capture for the capture process illustrated in FIG. 7A, as a function of the proportion of locking nucleic acids included in the capture probe, at three different temperatures.

FIG. 7B illustrates three graphs showing experimental data for relative capture efficiency as a function of the number of LNA's in the 16mer capture probe, taken at three different experimental temperatures. As illustrated in the center of the three graphs, at 65° C., utilizing nine LNA's in the capture probe yielded the highest mean signal, which equates to the highest efficiency for capturing the amplified 22mers, while utilizing greater than or less than nine LNA's was less efficient. Further, at 80° C. and at 22° C. (room temperature), there was very little change in efficiency of capturing the amplified 22mers, and the overall efficiency using any number of LNA's at these temperatures was significantly decreased.

Thus, in certain embodiments, a preferred temperature of the reaction is at or near the $T_m$ of the capture probe. Further, in some embodiments, the temperature used during the described method is greater than the $T_m$ of the DNA or RNA product (such as the previously described 22mer reaction product), which in this example is approximately 50° C. Therefore, by adjusting the number of LNA's relative to the number of nucleotides in the capture probe, and setting the appropriate temperature of the mixture, capturing efficiency can be increased and/or optimized.

In one embodiment of the capture probe, at least 12 nucleotides are included. In non-exclusive alternative embodiments, at least 10, but not greater than 20 nucleotides are included in the capture probe. Still alternatively, the capture probe can include fewer than 10 or greater than 20 nucleotides. Further, in certain embodiments, less than approximately 75% of the nucleotides in the capture probe are locking nucleic acids. In non-exclusive alternative embodiments, less than approximately 90%, 62.5%, 50%, 40% or 25% of the nucleotides in the capture probe are locking nucleic acids. In other embodiments, at least 6, but not greater than 12 locking nucleic acids are included in the capture probe. In still alternative embodiments, fewer than 6 or greater than 12 locking nucleic acids can be included in the capture probe.

While the particular methods and compositions for amplification and/or capturing of nucleic acid sequences as shown and disclosed herein are fully capable of obtaining the objects and providing the advantages herein before stated, it is to be understood that it is merely illustrative of the presently preferred embodiments of the invention and that no limitations are intended to the details of the methods, construction or design herein shown and described.

What is claimed is:

1. A method for amplification and capture of nucleic acid sequences, the method comprising the steps of:
   annealing a forward primer to a DNA or RNA template;
   extending the forward primer using fewer than four different dNTPs to form an extended primer that terminates when an omitted dNTP is required for further extension of the forward primer;
   releasing the extended primer;
   exponentially amplifying the extended primer in a reaction vessel that includes a forward primer, a reverse primer, four different dNTPs and a capture probe, the capture probe including at least n oligonucleotides, wherein fewer than n of the oligonucleotides are locking nucleic acids; and
   concurrently capturing one of the extended primers in the reaction vessel with the capture probe while amplifying the extended primer.

2. The method of claim 1 wherein the steps of annealing, extending and releasing are all performed in a non-exponential manner.

3. The method of claim 1 wherein the step of annealing includes the forward primer having fewer than 12 bases.

4. The method of claim 1 wherein the step of annealing includes the forward primer having exactly 11 bases.

5. The method of claim 1 wherein the step of extending includes the extended primer having approximately 22 bases.

6. The method of claim 1 wherein the step of annealing includes using 3 dNTPs that are different from one another and one ddNTP.

7. The method of claim 1 wherein n equals 12.

8. The method of claim 7 wherein the number of locking nucleic acids is less than 75% of n.

9. The method of claim 1 wherein n equals greater than 14 and less than 18, and the number of locking nucleic acids is greater than 6 and less than 12.

10. A method for amplification and capture of nucleic acid sequences, the method comprising the steps of:
    annealing a forward primer to a DNA or RNA template;
    extending the forward primer using fewer than four different dNTPs to form an extended primer that terminates when an omitted dNTP is required for further extension of the forward primer;
    releasing the extended primer;
    exponentially amplifying the extended primer using a forward primer, a reverse primer and four different dNTPs; and
    capturing one of the amplified extended primers with a capture probe, the capture probe including at least n oligonucleotides, wherein fewer than n of the oligonucleotides are locking nucleic acids;
    wherein the steps of annealing, extending and releasing occur at a first reaction temperature that is substantially isothermal and in the absence of a helicase, and wherein the steps of exponentially amplifying and capturing occur at a second reaction temperature that is substantially isothermal.

11. The method of claim 10 wherein the steps of annealing, extending and releasing are all performed in a non-exponential manner.

12. The method of claim 10 wherein the step of annealing includes the forward primer having fewer than 12 bases.

13. The method of claim 10 wherein the step of annealing includes the forward primer having exactly 11 bases.

14. The method of claim 10 wherein the step of extending includes the extended primer having approximately 22 bases.

15. The method of claim 10 wherein the step of annealing includes using 3 dNTPs that are different from one another and one ddNTP.

16. The method of claim 10 wherein n equals 16.

17. The method of claim 16 wherein the number of locking nucleic acids is less than 62.5% of n.

18. The method of claim 10 wherein n equals greater than 14 and less than 18, and the number of locking nucleic acids is greater than 6 and less than 12.

19. The method of claim 10 wherein at least one of the reaction temperatures is within the range of between 60° C and 68° C.

20. The method of claim 19 wherein the first reaction temperature is substantially similar to the second reaction temperature.

21. The method of claim 10 wherein at least one of the reaction temperatures is approximately 65° C.

22. A method for amplification and capture of nucleic acid sequences, the method comprising the steps of:
    annealing a forward primer to a DNA or RNA template;
    extending the forward primer using fewer than four different dNTPs to form an extended primer that terminates when an omitted dNTP is required for further extension of the forward primer;
    releasing the extended primer;
    exponentially amplifying the extended primer in a reaction vessel that includes a forward primer, a reverse primer, four different dNTPs and a capture probe; and
    concurrently capturing one of the extended primers in the reaction vessel with the capture probe while amplifying the extended primer;
    wherein the steps of annealing, extending and releasing occur at a first reaction temperature that is substantially isothermal and in the absence of a helicase, and wherein the steps of exponentially amplifying and capturing occur at a second reaction temperature that is substantially isothermal.

23. The method of claim 22 wherein the steps of annealing, extending and releasing are all performed in a non-exponential manner.

24. The method of claim 22 wherein the step of annealing includes the forward primer having fewer than 12 bases.

25. The method of claim 22 wherein the step of annealing includes the forward primer having exactly 11 bases.

26. The method of claim 22 wherein the step of extending includes the extended primer having approximately 22 bases.

27. The method of claim 22 wherein the step of annealing includes using 3 dNTPs that are different from one another and one ddNTP.

28. The method of claim 22 wherein n equals 16.

29. The method of claim 22 wherein the number of locking nucleic acids is less than 62.5% of n.

30. The method of claim 22 wherein n equals greater than 14 and less than 18, and the number of locking nucleic acids is greater than 6 and less than 12.

31. The method of claim 22 wherein at least one of the reaction temperatures is within the range of between 60° C. and 68° C.

32. The method of claim 31 wherein the first reaction temperature is substantially similar to the second reaction temperature.

33. The method of claim 22 wherein at least one of the reaction temperatures is approximately 65° C.

34. A method for amplification and capture of nucleic acid sequences, the method comprising the steps of:
   annealing a forward primer to a DNA or RNA template;
   extending the forward primer using fewer than four different dNTPs to form an extended primer that terminates when an omitted dNTP is required for further extension of the forward primer;
   releasing the extended primer;
   exponentially amplifying the extended primer in a reaction vessel that includes a forward primer, a reverse primer, four different dNTPs and a capture probe, the capture probe including n oligonucleotides, wherein fewer than n of the oligonucleotides are locking nucleic acids; and
   concurrently capturing one of the extended primers in the reaction vessel with the capture probe while amplifying the extended primer;
   wherein the steps of annealing, extending and releasing occur at a first reaction temperature that is substantially isothermal and in the absence of a helicase, and wherein the steps of exponentially amplifying and capturing occur at a second reaction temperature that is substantially isothermal.

35. The method of claim 34 wherein the steps of annealing, extending and releasing are all performed in a non-exponential manner.

36. The method of claim 34 wherein the step of annealing includes the forward primer having approximately 11 bases.

37. The method of claim 36 wherein the step of extending includes the extended primer having approximately 22 bases.

38. The method of claim 34 wherein the step of annealing includes using 3 dNTPs that are different from one another and one ddNTP.

39. The method of claim 34 wherein n equals 16.

40. The method of claim 39 wherein the number of locking nucleic acids is less than 62.5% of n.

41. The method of claim 34 wherein n equals greater than 14 and less than 18, and the number of locking nucleic acids is greater than 6 and less than 12.

42. The method of claim 34 wherein at least one of the reaction temperatures is within the range of between 60° C. and 68° C.

43. The method of claim 42 wherein the first reaction temperature is substantially similar to the second reaction temperature.

44. The method of claim 34 wherein at least one of the reaction temperatures is approximately 65° C.

45. The method of claim 34 wherein each of the reaction temperatures is approximately 65° C.

* * * * *